(12) United States Patent
McCauley

(10) Patent No.: US 9,874,546 B2
(45) Date of Patent: Jan. 23, 2018

(54) SYSTEMS AND METHODS FOR CONSERVING CARRIER GAS

(71) Applicant: Thermo Finnigan LLC, San Jose, CA (US)

(72) Inventor: Edward B. McCauley, Cedar Park, TX (US)

(73) Assignee: Thermo Finnigan LLC, San Jose, CA (US)

( * ) Notice: Subject to any disclaimer, the term of this patent is extended or adjusted under 35 U.S.C. 154(b) by 251 days.

(21) Appl. No.: 14/808,657

(22) Filed: Jul. 24, 2015

(65) Prior Publication Data
US 2017/0023534 A1  Jan. 26, 2017

(51) Int. Cl.
*G01N 30/02* (2006.01)
*G01N 30/18* (2006.01)
*G01N 30/12* (2006.01)
*G01N 30/32* (2006.01)

(52) U.S. Cl.
CPC ....... *G01N 30/18* (2013.01); *G01N 2030/025* (2013.01); *G01N 2030/127* (2013.01); *G01N 2030/324* (2013.01)

(58) Field of Classification Search
USPC ........................................................ 73/23.37
See application file for complete search history.

(56) References Cited

U.S. PATENT DOCUMENTS

| | | | | |
|---|---|---|---|---|
| 4,440,013 A * | 4/1984 | Adams | ................... | G01N 30/74 250/343 |
| 4,587,835 A * | 5/1986 | Adams | ................... | G01N 30/74 250/343 |
| 4,713,963 A * | 12/1987 | Sharp | ................. | G01N 30/7206 73/23.37 |
| 5,012,052 A * | 4/1991 | Hayes | ................ | G01N 30/7206 250/282 |
| 6,006,584 A * | 12/1999 | Itoi | .................... | G01N 30/7206 250/288 |
| 6,351,983 B1 * | 3/2002 | Haas | .................. | G01N 30/7206 250/281 |
| 8,371,152 B2 | 2/2013 | McCauley et al. | | |

(Continued)

OTHER PUBLICATIONS

McCauley, et al., "Gas Chromatograph System Employing Hydrogen Carrier Gas," U.S. Appl. No. 14/334,282, filed Jul. 17, 2014 (specification, claims, abstract, and drawings only), pp. 1-22.

*Primary Examiner* — Eric S McCall
*Assistant Examiner* — Mohammed E Keramet-Amircola
(74) *Attorney, Agent, or Firm* — David A. Schell

(57) ABSTRACT

A device for a gas chromatograph system includes an injector, a conduit assembly, a flow restrictor, and a pressure controller. The injector is connected to a carrier gas source and an auxiliary gas source. The conduit assembly surrounds the input end of an analytical column. A carrier gas is supplied at a constant pressure through a flow restrictor to the injector. A pressure controller is configured to control the pressure of an auxiliary gas supplied to the injector from the auxiliary source. The pressure controller is configured to operate in a first mode to provide a first auxiliary gas pressure sufficient to force a flow of the auxiliary gas and a sample onto the analytical column during an inject phase and to operate in a second mode to provide a second auxiliary gas pressure below a threshold necessary to flow auxiliary gas into the analytical column during a resolving phase.

31 Claims, 10 Drawing Sheets

(56) References Cited

U.S. PATENT DOCUMENTS

| | | | |
|---|---|---|---|
| 2006/0123883 A1* | 6/2006 | Miyagawa | G01N 30/466 73/23.37 |
| 2007/0271997 A1* | 11/2007 | O'Brien | G01N 1/2202 73/23.37 |
| 2009/0199620 A1* | 8/2009 | Kawana | G01N 30/8603 73/23.37 |
| 2010/0101304 A1* | 4/2010 | McIntyre | G01N 30/7206 73/23.37 |
| 2010/0101411 A1* | 4/2010 | Tipler | G01N 30/20 95/86 |
| 2011/0192215 A1* | 8/2011 | Finlay | B01D 53/1412 73/23.37 |
| 2012/0103064 A1* | 5/2012 | McCauley | G01N 30/10 73/23.42 |
| 2014/0250978 A1* | 9/2014 | McCauley | G01N 30/16 73/23.39 |
| 2015/0059439 A1* | 3/2015 | Tipler | G01N 30/463 73/23.37 |
| 2016/0013037 A1* | 1/2016 | Jorabchi | H01J 49/105 73/23.37 |

* cited by examiner

SYSTEMS AND METHODS FOR CONSERVING CARRIER GAS

FIELD

The present disclosure generally relates to the field of gas chromatography including systems and methods for conserving carrier gas.

INTRODUCTION

Traditional split/splitless (SSL) or programmed temperature vaporizing (PTV) injection ports for gas chromatographs typically consume large volumes of carrier gas by virtue of what is used at the split vent and septum purge vent rather than what is utilized for the actual analytical separation (column flow). For example, a capillary column flow of approximately 1 standard cubic centimeter per minute (sccm) may have 50 sccm or more of split flow and 5 sccm of septum purge flow. One prior art method to reduce this consumption, e.g. "gas saver", can reduce the split flow following an injection period. Reducing the split flow to too low a value however can result in undesirable elevated baselines. This may be caused by a continual outgassing of higher molecular weight contaminants introduced from the sample matrix, outgassing of polymeric seals such as O-rings, injection port septa and/or coring of such septa, or be caused by oxidation of the column stationary phase due to larger concentrations of oxygen which has back-diffused through the septum. Reducing these contaminants has traditionally been accomplished through dilution by using large split flows.

Helium is becoming increasingly expensive and difficult to procure in some areas of the world. Helium is often the preferred carrier gas due to sensitivity, efficiency, chemical inertness, safety or other concerns. The consumption of high purity helium for split/purge flow can be a significant portion of the overall consumption of carrier gas. Additionally, maintaining the purity of the high purity carrier gas flowing into the analytical column can be critical to data quality. As such, minimizing the number of connections, valves, switches, and the like that can be potential sources of outgassing of contaminants along the flow path of the high purity carrier gas is desirable.

From the foregoing it will be appreciated that a need exists for improved systems and methods for conserving carrier gas.

SUMMARY

In a first aspect, a device for a gas chromatograph system can include an injector, a conduit assembly, a flow restrictor, and a pressure controller. The injector can be connected to a carrier gas source and an auxiliary gas source. The conduit assembly can surround the input end of an analytical column. A carrier gas can be supplied to the injector from the carrier gas source at a constant pressure through a flow restrictor. The pressure controller can be configured to control the pressure of an auxiliary gas supplied to the injector from the auxiliary source. The pressure controller can be configured to operate in a first mode to provide a first auxiliary gas pressure sufficient to force a flow of the auxiliary gas and a sample onto the analytical column during an inject phase and to operate in a second mode to provide a second auxiliary gas pressure below a threshold necessary to flow auxiliary gas into the analytical column during a resolving phase.

In various embodiments of the first aspect, the carrier gas can include He or $H_2$.

In various embodiments of the first aspect, the auxiliary gas can include $N_2$ or Ar.

In various embodiments of the first aspect, the flow restrictor is sized to provide a volume of carrier gas sufficient to prevent the auxiliary gas from entering the analytical column when the pressure control is operating in the second mode.

In various embodiments of the first aspect, the flow restrictor is sized to provide a volume of carrier gas that exceeds the operating flow of the analytical column by a factor of at least about 1.5. In particular embodiments, the flow restrictor is sized to provide a volume of carrier gas that exceeds the operating flow of the analytical column by a factor of at least about 2. In particular embodiments, the flow restrictor is sized to provide a volume of carrier gas that exceeds the operating flow of the analytical column by a factor of at least about 4.

In various embodiments of the first aspect, the flow restrictor is sized to provide a volume of carrier gas that exceeds the operating flow of the analytical column by a factor of not more than about 10. In particular embodiments, the flow restrictor is sized to provide a volume of carrier gas that exceeds the operating flow of the analytical column by a factor of not more than about 5.

In various embodiments of the first aspect, the flow restrictor provides a volume of carrier gas between about 1.0 sccm and about 10 sccm. In particular embodiments, the flow restrictor provides a volume of carrier gas between about 2 sccm and about 5 sccm.

In various embodiments of the first aspect, the injector is a split/splitless (SSL) injector.

In various embodiments of the first aspect, the injector is a programmed temperature vaporization (PTV) injector.

In a second aspect, a gas chromatograph system can include an analytical column, a detector, an injector, a conduit assembly, a flow restrictor, and a pressure controller. The detector can be coupled to an output end of the analytical column. The injector can be connected to a carrier gas source and an auxiliary gas source. The conduit assembly can surround the input end of an analytical column. A carrier gas can be supplied from the carrier gas source at a substantially constant pressure through the flow restrictor to the injector. The pressure controller can be configured to control the pressure of an auxiliary gas supplied to the injector from the auxiliary source. The pressure controller can be configured to provide a first auxiliary gas pressure sufficient to force a flow of the auxiliary gas and a sample onto the analytical column during an inject phase and a second auxiliary gas pressure below a threshold necessary to flow auxiliary gas into the analytical column during a resolving phase.

In various embodiments of the second aspect, the detector is a mass spectrometer.

In various embodiments of the second aspect, the injector is a split/splitless (SSL) injector.

In various embodiments of the second aspect, the injector is a programmed temperature vaporization (PTV) injector.

In various embodiments of the second aspect, the carrier gas includes He or $H_2$.

In various embodiments of the second aspect, the auxiliary gas includes $N_2$ or Ar.

In various embodiments of the second aspect, the flow restrictor is sized to provide a volume of carrier gas sufficient to prevent the auxiliary gas from entering the analytical column when the pressure control is operating in the second mode.

In various embodiments of the second aspect, the flow restrictor is sized to provide a volume of carrier gas that exceeds the operating flow of the analytical column by a factor of at least about 1.5.

In various embodiments of the second aspect, the flow restrictor is sized to provide a volume of carrier gas that exceeds the operating flow of the analytical column by a factor of not more than about 10.

In various embodiments of the second aspect, the flow restrictor provides a volume of carrier gas between about 1.0 sccm and about 10 sccm.

In a third aspect, a method for supplying a carrier gas to a gas chromatograph can include providing a carrier gas flow and an auxiliary gas flow to an injector. The carrier gas flow can be at a substantially fixed pressure and passing through a flow restrictor. The method can further include changing an auxiliary gas pressure during an inject phase to a first pressure sufficient to force at least a portion of the auxiliary gas flow and at least a portion of a sample onto an analytical column, and changing an auxiliary gas pressure during an resolving phase to an operating pressure of the analytical column. Additionally, the method can include resolving at least two compounds of the sample with the analytical column, and detecting the at least two compounds exiting the analytical column.

In various embodiments of the third aspect, the detector is a mass spectrometer.

In various embodiments of the third aspect, the carrier gas includes He or $H_2$.

In various embodiments of the third aspect, the auxiliary gas includes $N_2$, Ar, or $H_2$.

In various embodiments of the third aspect, the flow restrictor is sized to provide a volume of carrier gas sufficient to prevent the auxiliary from entering the analytical column during the resolving phase.

In various embodiments of the third aspect, the flow restrictor is sized to provide a volume of carrier gas that exceeds the operating flow of the analytical column by a factor of at least about 1.5.

In various embodiments of the third aspect, the flow restrictor is sized to provide a volume of carrier gas that exceeds the operating flow of the analytical column by a factor of not more than about 10.

In various embodiments of the third aspect, the flow restrictor provides a volume of carrier gas between about 1.0 sccm and about 10 sccm.

DRAWINGS

For a more complete understanding of the principles disclosed herein, and the advantages thereof, reference is now made to the following descriptions taken in conjunction with the accompanying drawings, in which.

Figure 1:
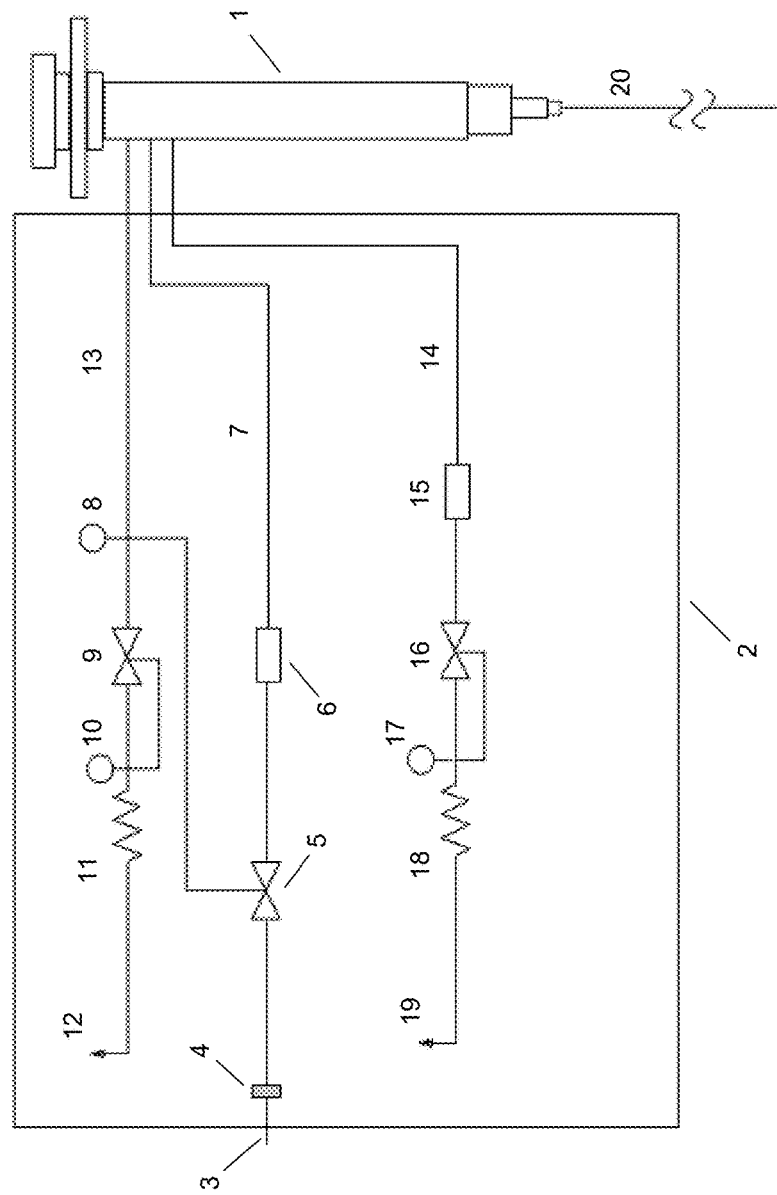
FIG. 1 is a diagram of an exemplary split/splitless injection system for a gas chromatograph.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DESCRIPTION OF VARIOUS EMBODIMENTS

Embodiments of systems and methods for conserving carrier gas are described herein.

The section headings used herein are for organizational purposes only and are not to be construed as limiting the described subject matter in any way.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and internet web pages are expressly incorporated by reference in their entirety for any purpose. Unless described otherwise, all technical and scientific terms used herein have a meaning as is commonly understood by one of ordinary skill in the art to which the various embodiments described herein belongs.

It will be appreciated that there is an implied "about" prior to the temperatures, concentrations, times, pressures, flow rates, cross-sectional areas, etc. discussed in the present teachings, such that slight and insubstantial deviations are within the scope of the present teachings. In this application, the use of the singular includes the plural unless specifically stated otherwise. Also, the use of "comprise", "comprises", "comprising", "contain", "contains", "containing", "include", "includes", and "including" are not intended to be limiting. It is to be understood that both the foregoing general description and the following detailed description are exemplary and explanatory only and are not restrictive of the present teachings.

As used herein, "a" or "an" also may refer to "at least one" or "one or more." Also, the use of "or" is inclusive, such that the phrase "A or B" is true when "A" is true, "B" is true, or both "A" and "B" are true. Further, unless otherwise required by context, singular terms shall include pluralities and plural terms shall include the singular.

A "system" sets forth a set of components, real or abstract, comprising a whole where each component interacts with or is related to at least one other component within the whole.

Helium is often used as a carrier gas for gas chromatography, due to the advantages of helium in areas of sensitivity, efficiency, chemical inertness, and safety. However, the costs for high purity helium are increasing and supplies are limited. As a result, high purity helium can be difficult to procure in some areas of the world. While hydrogen can also be used as a carrier gas, hydrogen can react with the sample in the heated injector as the sample is vaporized. Additionally, the employment of a mass spectrometer as a detector for a gas chromatograph can be problematic when using hydrogen. Poorer pumping speed, non-classical electron ionization (EI) spectra, altered response factors and retention time changes are amongst the problematic issues encountered.

In various embodiments, carrier gas can be supplied to an analytical column separate from an auxiliary gas used to provide a split/purge flow through the injector. Advantageously, this can significantly reduce the consumption of an expensive carrier gas such as high purity helium. Additionally, the sample can be substantially isolated from the carrier gas while in the heated injector, thereby reducing the reactivity with a carrier gas such as hydrogen.

In various embodiments, the analytical column flow can be regulated by the pressure of the auxiliary gas within the injector. By providing a restricted flow of the carrier gas that is slightly greater than the analytical column flow, the auxiliary gas can be substantially excluded from the analytical column during separation. During injection, a pressure surge of the auxiliary gas within the injector can be used to load the sample into the analytical column.

FIG. 1 illustrates a typical gas chromatograph inlet system. The system includes a split/splitless (SSL) injector 1 for injecting liquid samples. A carrier gas is delivered via an electronic pressure controller 2 to the injector 1. A gas supply, e.g. helium, is introduced under pressure to a gas fitting 3. A fine porosity filter 4, e.g. a stainless steel frit, removes any particulate matter that may foul operation of the proportional valve 5. The proportional valve 5 maintains a setpoint pressure within the body of the injector to establish a calculated flow in the analytical column 20. The proportional valve 5 can be controlled by sensing the pressure of the injector using a pressure sensor that provides a feedback loop to the control circuit (not shown). Optionally, a chemical trap 6 is included to scrub the carrier gas of potential contaminants, e.g. hydrocarbons and/or oxygen. Additional proportional valves 9, 16 allow purging and venting of some of the delivered carrier gas from the septum purge vent 12 and split vent 19 respectively, by calculation of the pressure drop across restrictors 11, 18.

In the split injection mode, a split flow is established that exits the split line 14. This mode is used for injection of concentrated analytes to prevent overloading of the column or saturation of the detection system used at the terminal end of the column.

In the splitless mode of operation, the split line 14 is closed during injection to cause the bulk of the sample material to be transferred to the capillary column 20. After a specified time interval, the split vent is opened to vent residual solvent vapors and to dilute any contaminants that might outgas from contaminated surfaces.

In both modes, far greater amounts of carrier gas are used for split flow and septum purge flow than are required for the gas chromatography (GC) column flow carrying out the analytical separation. Following a split or splitless injection, large volumes of split flow are typically maintained to dilute outgassing of residual contaminants. This results in a large consumption of high purity carrier gas, such as helium.

Figure 2:
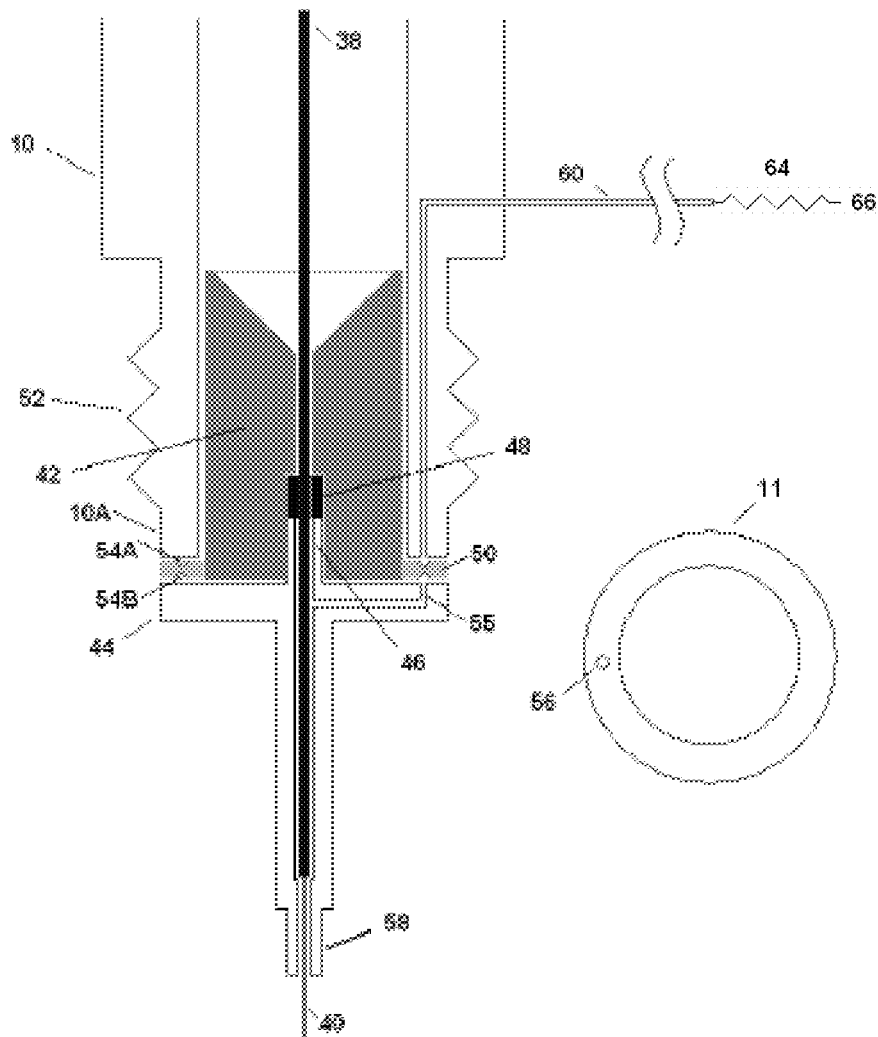
FIGS. 2 and 3 are diagrams of an exemplary split/splitless injection system for a gas chromatography instrument, in accordance with various embodiments.

FIG. 2 illustrates an embodiment of a carrier gas conservation device for use with a modified SSL injector. The lower portion of an SSL injector is designed to allow helium gas to be selectively passed over the end of an analytical column. A gas other than helium is introduced to the injector in a conventional manner in order to pressurize the inlet and provide split flow and septum purge flow. The novel SSL injector body may be used in the system disclosed in FIG. 1.

The upper end of a conduit, e.g. short segment of deactivated fused silica tubing 38 is positioned within the confines of an injection port liner (not shown). Positioned within the tubing 38 is the analytical column 40. A liner support 42 and base 44 are screwed together at the threaded stem 46 to allow compression of the encapsulated graphite ferrule 48. This maintains a gas tight seal between the fused silica tubing 38 and the base 44. A soft metallic gasket 50 is positioned between the base 44 and terminal end of the injector 10A to create a seal between base 44 and the injector body 10. A retaining nut (not shown) secures the base 44 to the threaded portion 52 of injector body 10.

The short segment of fused silica tubing 38 is selected to have an internal diameter slightly larger than the outer diameter of the analytical column 40. For example, Megabore tubing of 0.53 mm ID is suitable for most analytical columns with internal diameters of 0.25 or 0.32 mm ID. Preferably the tubing has been deactivated and contains no stationary phase. This segment of tubing alternatively can be fabricated from glass lined stainless steel tubing, Silcosteel® tubing, or other suitably inert material.

In this illustrative example, the analytical column 40 extends preferably to within 1 cm of the uppermost end of the tubing 38. This allows locating the column entrance within the hot injector body, minimizes void volume effects and allows a sufficient back diffusion barrier to the auxiliary gas during analysis. The gasket 50 includes a pair of gas channels 54A, 54B in the form of an annular groove cut on each face of the metallic gasket 50. The gasket 50 shown in top view as 11 also includes a hole 56 located on the centerline of gasket 50 to create a fluid communication between the upper and lower groove channels 54A, 54B. The terminal end 58 of base 44 is threaded so that a retaining nut and ferrule (not shown for simplicity) can create a seal between the analytical column 40 and the base 44. A conduit 60 supplies a flow of helium to the upper groove channel 54A. The helium flows around the upper groove channel until it finds hole 56. It then passes through hole 56 into the lower groove channel 54B and into base 44 at entrance point 55. The base 44 allows the helium to flow downward around the outside of the fused silica tube 38 to sweep void volume then proceed upward into tube 38 and finally the injector interior after passing the input end of the analytical column 40. The flow established into the conduit 60 should be slightly higher than the calculated column flow delivered to column 40 following the injection period. To illustrate, 2 sccm of conduit flow could be used for calculated column flows of 1 sccm.

The flow through a GC capillary column is typically established by setting an inlet pressure. The flow can be calculated and thereby controlled using prior knowledge of the gas viscosity, column dimensions and inlet and outlet pressures using the Poiseuille equation:

$$\frac{dV}{dT} = \frac{\pi r^4}{16\eta L}\left(\frac{(p_i^2 - p_o^2)}{p_o}\right) \qquad \text{Equation 1}$$

where:
$P_i$ inlet pressure
$P_o$ outlet pressure
L is the length of the column
$\eta$ is the viscosity of the gas r is the column internal radius Since the inlet pressure is known, the conduit 60 can be connected to a flow restrictor 64 of known dimensions external to the oven (not shown) proper, so that a pressure can be set upstream of it to affect a flow of helium across the input end of the analytical column. The low pressure drop which results in the ~1 cm length of 0.53 mm ID tubing near the end of the column ensures that the electronic pressure control is maintained resulting in nearly identical retention times as prior art methods. The electronic pressure control (EPC) functionality is not impaired by the operation of helium delivery to tube 38 of FIG. 2. The flow of helium to the column is maintained by the head pressure of the auxiliary gas in the injector, while the excess helium is simply diverted upward into the injector where it contributes to the bulk auxiliary gas purge. The inert nature of the deactivated fused silica tube 38 along with its short length ensure minimal surface activity and efficient sample transfer.

In this illustrative example, the conduit 60 may comprise a 304 stainless steel tube of 0.9 mm OD×0.5 mm ID×300 mm length. The conduit is attached to the hot injector body 10 and the opposite end attaches to capillary restrictor 64 mounted external to the GC oven (not shown) at ambient temperature. The capillary restrictor 64 can have an internal diameter of 50 microns and be 500 mm in length. When restrictor 64 is pressurized to 100 psig at the inlet end 66, a helium flow of 2.8 sccm will be established when the injector is operated near ambient pressure. The injector 10 can be operated at higher pressures without undue drop in the restrictor flow, since the restrictor input is maintained at relatively high pressure. This simplifies the implementation of the hardware. Increasing the injector pressure to 30 psig for example will reduce the restrictor flow to 2.4 sccm allowing sufficient flow for both the analysis (1.0 sccm) and the prevention of significant back diffusion for small bore e.g. 0.25 mm ID analytical columns.

During injection of a sample into the injector 10 of FIG. 2, the injector pressure can be further increased to limit the flow of carrier gas through restrictor 64 and increase the column flow. The auxiliary gas will then sweep sample components onto the analytical column 40. Following the injection of the sample and sample transfer to the analytical column 40, the injector pressure is decreased to re-establish a carrier gas flow sufficient to limit auxiliary gas from entering the analytical column 10 so that the chromatographic process utilizes helium for the bulk of the analytical separation, while the auxiliary gas is used to purge the injector.

The embodiment of FIG. 2 uses hardware that may be removed from the system for maintenance and column positioning purposes while also allowing re-assembly which is immune to rotational positioning of the components. This provides significant ease-of-use.

The flow of helium to the conduit 60 can be established by any means known in the current art including but not limited to programmable pressure and/or flow controllers, manual pneumatic controllers and regulators, secondary inlet pressure controllers e.g. (from a secondary GC inlet pneumatic module pressurizing a calibrated restrictor). Alternate configurations allowing helium flow to be used as the auxiliary gas during the injection period are also possible if configured, but will result in higher helium consumption.

The flow delivered by the conduit 60 can be calculated using a mathematical model, or optimized empirically by adjusting the flow while monitoring the presence of auxiliary gas in the gas delivered to column 40. To illustrate, if nitrogen is the auxiliary gas delivered to the injector, and the detection system employs a mass spectrometer, the air/water spectrum can be monitored for the abundance of nitrogen in the column effluent. The helium flow can be adjusted accordingly to minimize consumption of helium while preventing undue back diffusion of nitrogen into the column.

Figure 3:
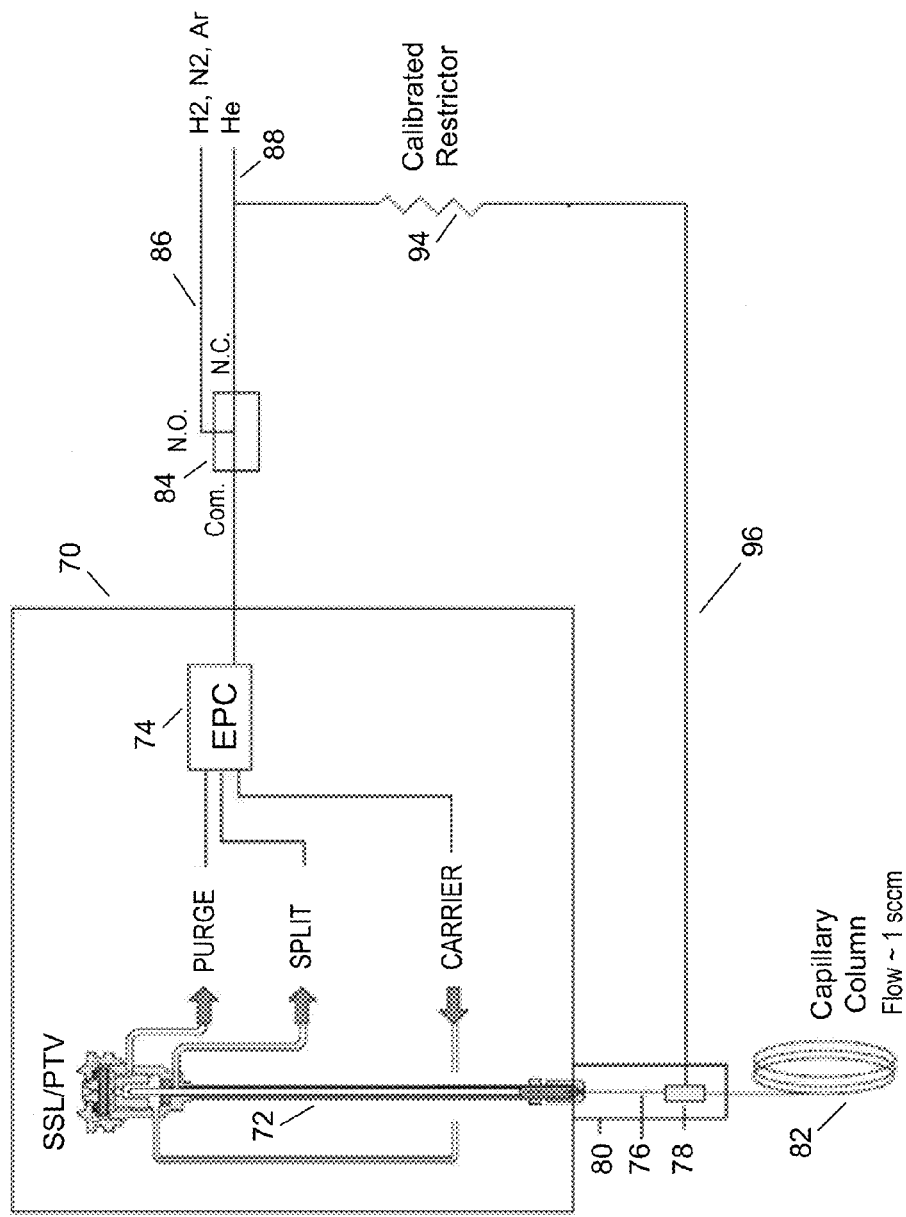

FIG. 3 illustrates an embodiment of a carrier gas conservation device for use with an unmodified PTV or SSL injector, such as on an existing gas chromatograph. An inlet system 70 comprising a PTV or SSL injector 72 and electronic flow controller 74 is outfitted with a short segment of pre-column 76 and low-dead-volume tee piece 78 housed in a small heated zone 80. The temperature control of heated zone 80 can be provided by an external controller or by an unused auxiliary heater channel as is often found on typical GC systems. The pre-column 76 is preferably as short as possible and comprises a few centimeter length of 0.53 mm ID fused silica tubing, steel clad fused silica tubing, glass lined stainless steel tubing, or the like. The inlet of analytical column 82 should pass through tee-piece 78 and terminate within the heated pre-column 76 preferably within one centimeter of the uppermost end. A 3-way solenoid selection valve 84 allows selection of one of an auxiliary gas at feed point 86 or a carrier gas source, such as helium or hydrogen, delivered at feed point 88. The valve 84 allows (optionally) selection between the carrier gas and an auxiliary gas during the injection period. The three-way valve 84 can alternatively comprise a pair of on/off valves if superior isolation between the carrier gas and the auxiliary gas is desired. A capillary restrictor 94 is disposed in the flow path of conduit 96 for delivering a carrier gas flow that is greater than the analytical column flow, such as about 2.0 sccm. The dimensions of the restrictors can be selected based on the input pressure of feed point 88 to establish a given flow range based on the pressure swing of injector 72. The actual flow can vary, e.g. 2-4 sccm without affecting performance. Activation of solenoid valve 84 can be accomplished using the time events programming features of most modern day gas chromatographs.

Embodiments using helium as a carrier gas and nitrogen as the auxiliary gas are preferred. Nitrogen has a viscosity similar enough to helium to allow proper flow control of many existing septum purge and split vent hardware configurations on existing in-field chromatographs without modification. The similar viscosity also allows proper sample loading during injection. Using a commercially available hydrogen or nitrogen gas generator along with embodiments of the present invention also allow for a large reduction in the number of high pressure cylinders and/or the frequency with which they need to be replaced. Argon can also be beneficially employed as a low cost inert gas delivered either via a high pressure cylinder or as a gas from the gas output valve of a liquid argon Dewar.

It is also envisioned that gas types not generally employed to pressurize GC inlets could also potentially be used. For example, liquefiable gasses such as carbon dioxide are low cost, and large gas volumes are available per cylinder since the gas exists in liquid form within the confines of the cylinder.

Method

Figure 4:
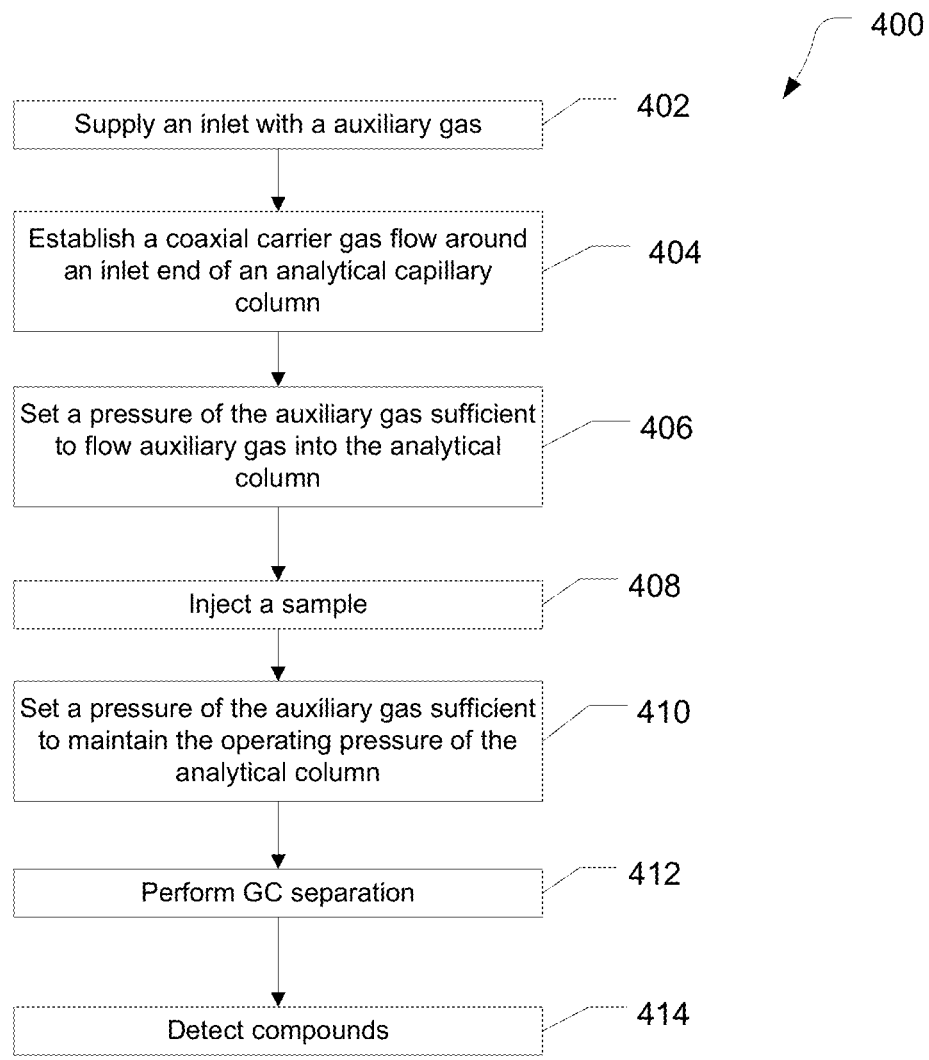
FIG. 4 is a flow diagram of an exemplary method for operating a gas chromatography instrument, in accordance with various embodiments.

FIG. 4 shows a flow diagram for the operation of the gas chromatograph using a carrier gas conservation device. At 402, the inlet is supplied with an auxiliary gas. In step 404, a coaxial carrier gas flow is established around an inlet end of an analytical column. In various embodiments, the carrier gas can be helium (He) or hydrogen ($H_2$). The carrier gas flow can be established by providing a pressurized flow of the carrier gas through a flow restrictor. The flow of the carrier gas through the restrictor can be larger than the column flow, such as by an amount sufficient to prevent the auxiliary gas from entering the analytical column during a separation or resolving period of the column operation. For example, the flow of the carrier gas can exceed the operational flow of the analytical column during separation by a factor of at least about 1.5, such as a factor of at least about 2, even a factor of at least about 4. In various embodiments, the flow through the restrictor may exceed the operational flow of the analytical column by a factor of not more than about 10, such as a factor of not more than about 5. In various embodiments, the flow restrictor can provide a volume of carrier gas between about 1 sccm and about 10 sccm, such as between about 2 sccm and about 5 sccm.

At 406, the pressure of the auxiliary gas can be increased to a pressure sufficient to flow the auxiliary gas and at least a portion of the sample into the column. In various embodiments, the auxiliary gas can be nitrogen or argon. In particular embodiments, hydrogen can be used as an auxiliary gas when helium is used as a carrier gas. At 408, a sample can be supplied to the injector. In various embodiments, the sample can be heated to vaporize the components. For a splitless injection, substantially all of the sample can enter the column during the injection period. Alternatively, for a split injection, only a portion of the sample can enter the column during the injection period, while the rest of the sample is flushed from the injector with the split gas flow.

At 410, after the injection period, the pressure of the auxiliary gas can be lowered to a pressure sufficient to maintain an operating flow of gas through the analytical column. While the auxiliary gas regulates the pressure of the analytical column, the flow of the carrier gas is sufficient that the gas flowing through the column consists of the carrier gas and is substantially free of the auxiliary gas.

At 412, components of the sample can be separated by the analytical column, and at 414, the components exiting the column can be detected and/or analyzed. In various embodiments, the components can be detected by various means, such as a flame ionization detector, a thermal conductivity detector, a mass spectrometer, or the like.

Results

Figure 5:
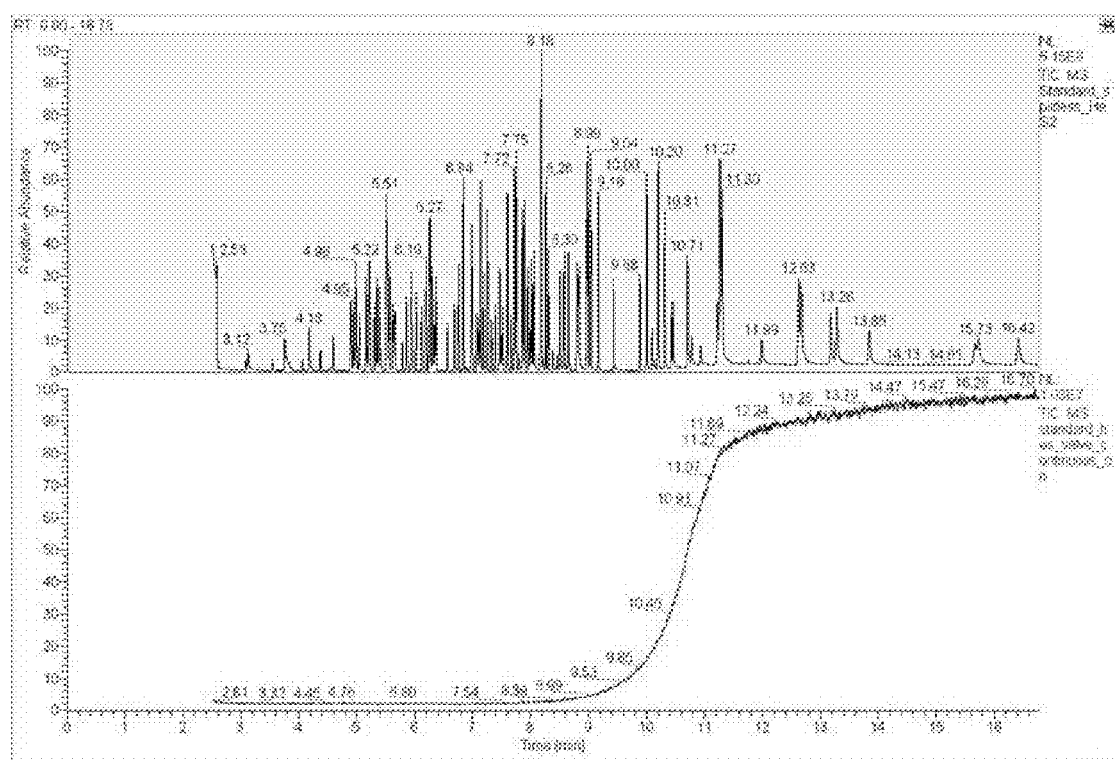
FIGS. 5 through 10 are exemplary data illustrating the use of an exemplary split/splitless injection system, in accordance with various embodiments.

FIG. 5 shows a comparison of a chromatogram from a splitless injection using helium only (top panel) with a chromatogram from a splitless injection using helium as a carrier gas and nitrogen as an auxiliary gas without a pressure surge during injection (bottom panel). The absence of peaks in the bottom panel is indicative that the helium carrier gas flow substantially prevented the sample from entering the analytical column during the injection.

Figure 6:
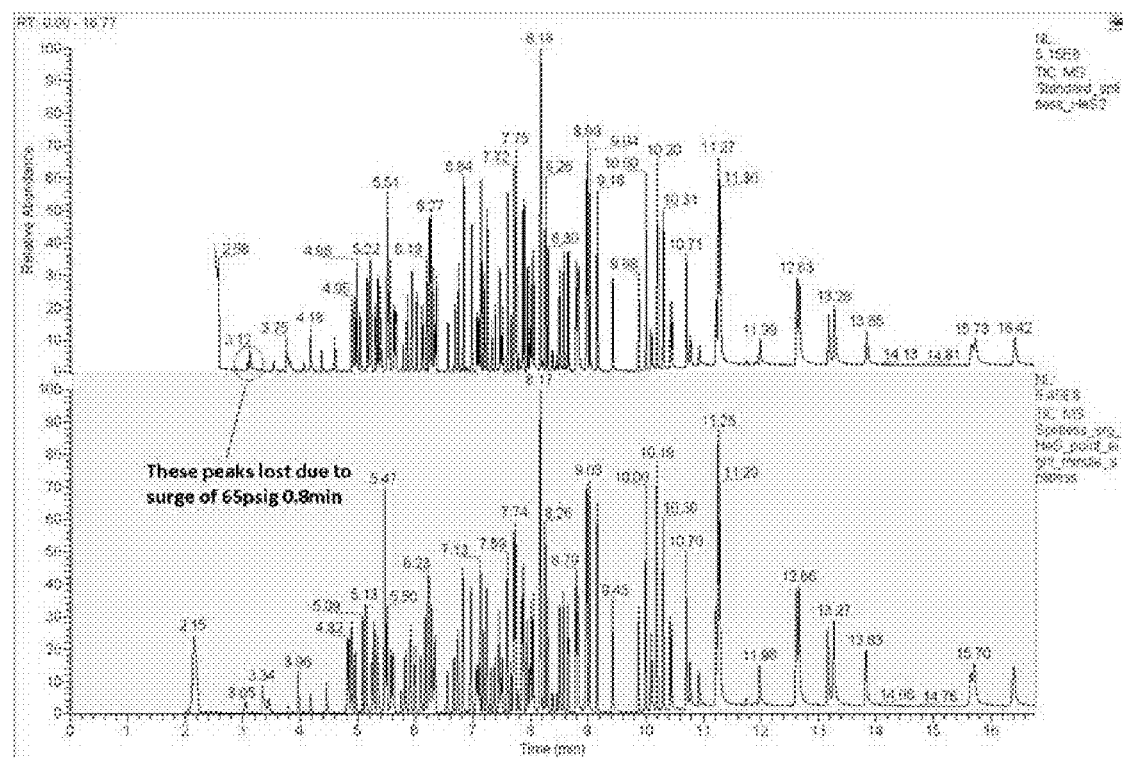

FIG. 6 shows a comparison of a chromatogram from a splitless injection using helium only (top panel) with a chromatogram from a splitless injection using helium as a carrier gas and nitrogen as an auxiliary gas with a pressure surge of 65 psig for 0.8 min during injection (bottom panel). The peaks in the bottom panel are substantially the same as the peaks in the top panel with the exception of a couple of early peaks. This is indicative that the pressure surge of 65 psig for 0.8 min was sufficient to inject the sample into the analytical column, but that early compounds are pushed through the column too quickly due to the increased flow rate of the column during the pressure surge.

Figure 7:
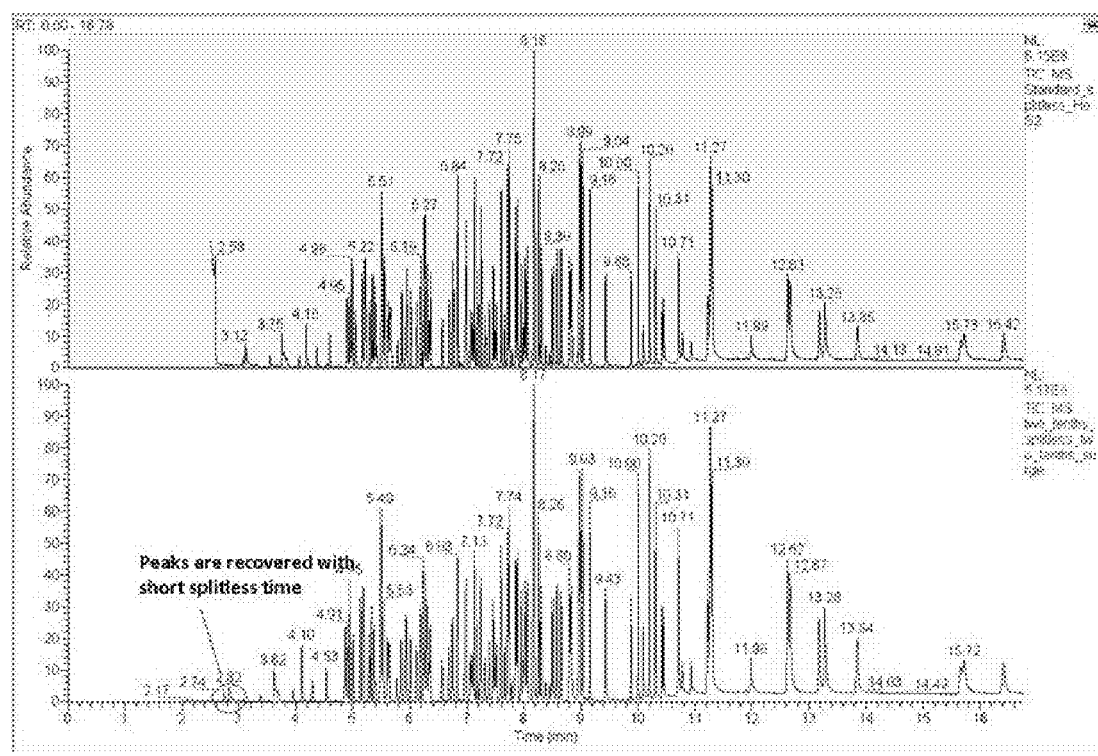
Figure 8:
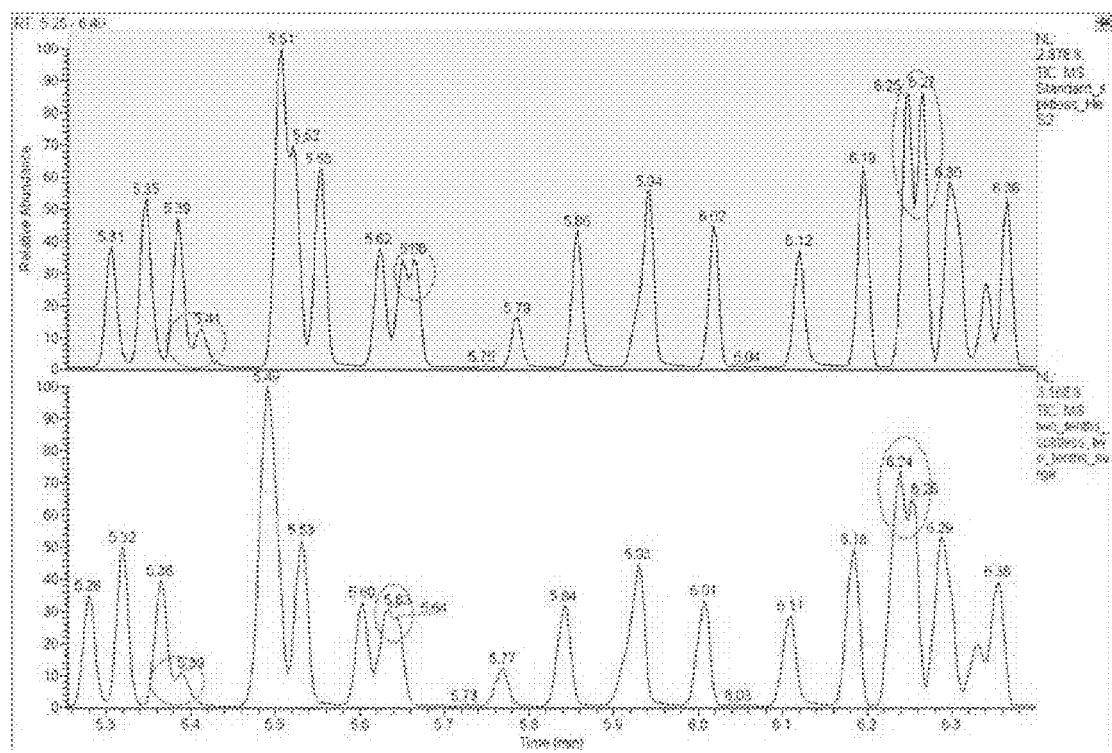

FIG. 7 shows comparisons of a chromatogram from a splitless injection using helium only (top panel) with a chromatogram from a splitless injection using helium as a carrier gas and nitrogen as an auxiliary gas with a pressure surge of 65 psig for 0.1 min during injection (bottom panel). As seen in FIG. 7, the early peaks are recovered with the shorter split time. However, the peaks are broadened relative to the helium only injection, as seen in the expanded view of FIG. 8.

Figure 9:
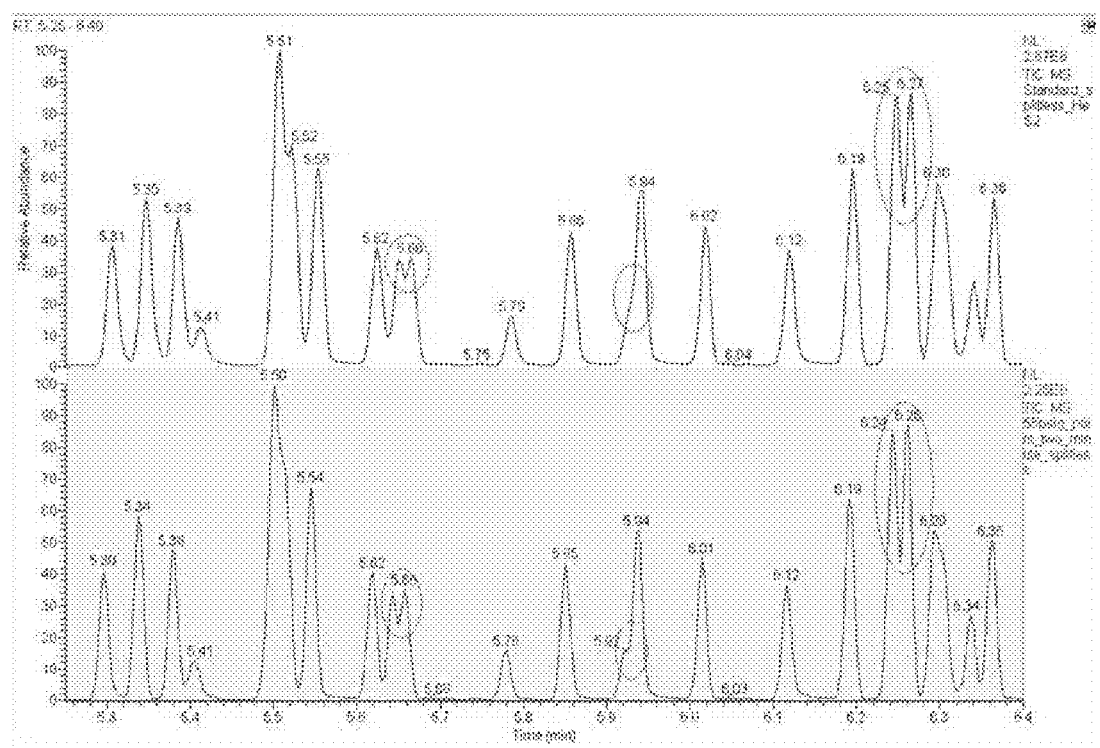

FIG. 9 shows a comparison of a chromatogram from a splitless injection using helium only (top panel) with a chromatogram from a splitless injection using a helium as a carrier gas and nitrogen as an auxiliary gas with a pressure surge of 55 psig for 0.1 min during injection (bottom panel). The separation achieved at 55 psig is comparable to the separation using helium only.

Figure 10:
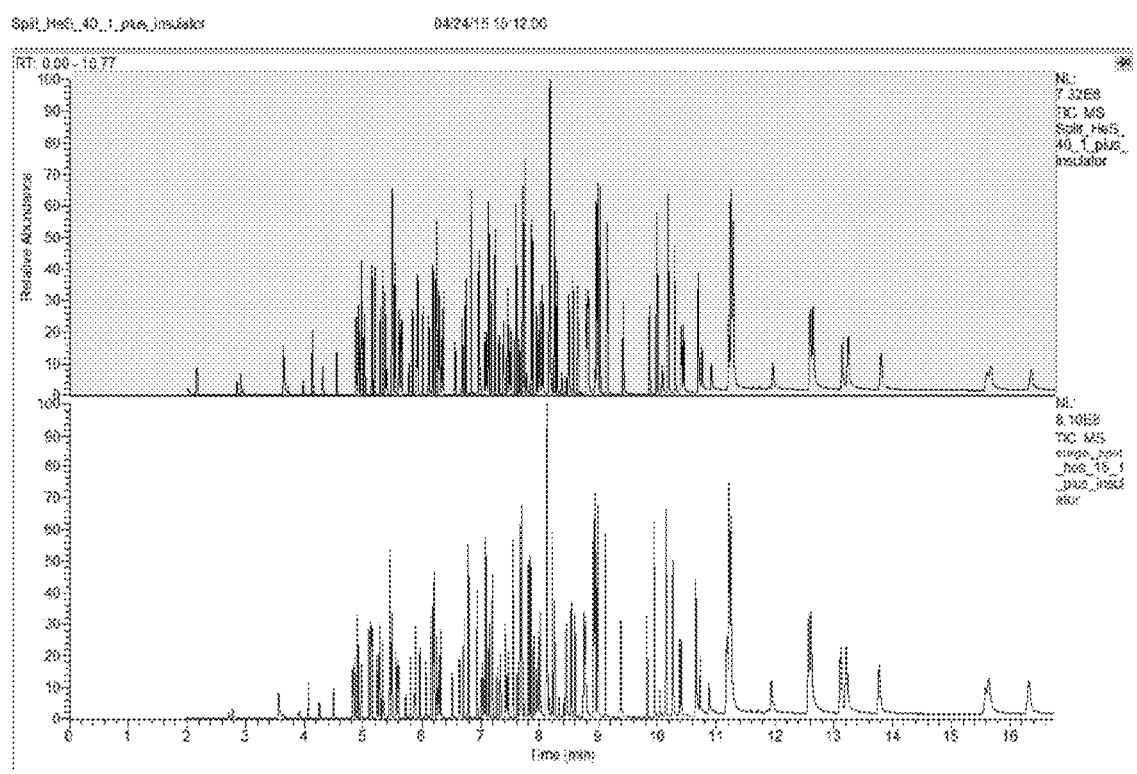

FIG. 10 shows a comparison of a chromatogram from a split injection using helium only (top panel) with a chromatogram from a split injection using helium as a carrier gas and nitrogen as an auxiliary gas with a pressure surge of 55 psig for 0.1 min during injection (bottom panel). The peaks in the bottom panel are substantially the same as the peaks in the top panel.

What is claimed is:

1. A device for a gas chromatograph system comprising:
   an injector connected to a carrier gas source and an auxiliary gas source;
   a conduit assembly surrounding the input end of an analytical column;
   a flow restrictor coupled to the conduit assembly through which a carrier gas is supplied to the injector from the carrier gas source at a constant pressure; and
   a pressure controller configured to control the pressure of an auxiliary gas supplied to the injector from the auxiliary source, the pressure controller configured to operate in a first mode to provide a first auxiliary gas pressure sufficient to force a flow of the auxiliary gas and a sample onto the analytical column during an inject phase and to operate in a second mode to provide a second auxiliary gas pressure below a threshold necessary to flow auxiliary gas into the analytical column during a resolving phase.

2. The device of claim 1, wherein the carrier gas includes He or $H_2$.

3. The device of claim 1, wherein the auxiliary gas includes $N_2$ or Ar.

4. The device of claim 1, wherein the flow restrictor is sized to provide a volume of carrier gas sufficient to prevent the auxiliary gas from entering the analytical column when the pressure control is operating in the second mode.

5. The device of claim 1, wherein the flow restrictor is sized to provide a volume of carrier gas that exceeds the operating flow of the analytical column by a factor of at least about 1.5.

6. The device of claim 5, wherein the flow restrictor is sized to provide a volume of carrier gas that exceeds the operating flow of the analytical column by a factor of at least about 2.

7. The device of claim 6, wherein the flow restrictor is sized to provide a volume of carrier gas that exceeds the operating flow of the analytical column by a factor of at least about 4.

8. The device of claim 1, wherein the flow restrictor is sized to provide a volume of carrier gas that exceeds the operating flow of the analytical column by a factor of not more than about 10.

9. The device of claim 8, wherein the flow restrictor is sized to provide a volume of carrier gas that exceeds the operating flow of the analytical column by a factor of not more than about 5.

10. The device of claim 1, wherein the flow restrictor provides a volume of carrier gas between about 1.0 sccm and about 10 sccm.

11. The device of claim 10, wherein the flow restrictor provides a volume of carrier gas between about 2 sccm and about 5 sccm.

12. The device of claim 1, wherein the injector is a split/splitless (SSL) injector.

13. The device of claim 1, wherein the injector is a programmed temperature vaporization (PTV) injector.

14. A gas chromatograph system comprising:
an analytical column;
a detector coupled to an output end of the analytical column;
an injector connected to a carrier gas source and an auxiliary gas source;
a conduit assembly surrounding the input end of an analytical column;
a flow restrictor coupled to the conduit assembly through which a carrier gas is supplied to the injector from the carrier gas source at a substantially constant pressure; and
a pressure controller configured to control the pressure of an auxiliary gas supplied to the injector from the auxiliary source, the pressure controller configured to provide a first auxiliary gas pressure sufficient to force a flow of the auxiliary gas and a sample onto the analytical column during an inject phase and a second auxiliary gas pressure below a threshold necessary to flow auxiliary gas into the analytical column during a resolving phase.

15. The system of claim 14, wherein the detector is a mass spectrometer.

16. The system of claim 14, wherein the injector is a split/splitless (SSL) injector.

17. The system of claim 14, wherein the injector is a programmed temperature vaporization (PTV) injector.

18. The system of claim 14, wherein the carrier gas includes He or $H_2$.

19. The system of claim 14, wherein the auxiliary gas includes $N_2$ or Ar.

20. The system of claim 14, wherein the flow restrictor is sized to provide a volume of carrier gas sufficient to prevent the auxiliary gas from entering the analytical column when the pressure control is operating in the second mode.

21. The system of claim 14, wherein the flow restrictor is sized to provide a volume of carrier gas that exceeds the operating flow of the analytical column by a factor of at least about 1.5.

22. The system of claim 14, wherein the flow restrictor is sized to provide a volume of carrier gas that exceeds the operating flow of the analytical column by a factor of not more than about 10.

23. The system of claim 14, wherein the flow restrictor provides a volume of carrier gas between about 1.0 sccm and about 10 sccm.

24. The method of claim 23, wherein the flow restrictor provides a volume of carrier gas between about 1.0 sccm and about 10 sccm.

25. A method for supplying a carrier gas to a gas chromatograph, comprising:
providing a carrier gas flow and an auxiliary gas flow to an injector, the carrier gas flow being at a substantially fixed pressure and passing through a flow restrictor;
changing an auxiliary gas pressure during an inject phase to a first pressure sufficient to force at least a portion of the auxiliary gas flow and at least a portion of a sample onto an analytical column;
changing an auxiliary gas pressure during an resolving phase to an operating pressure of the analytical column;
resolving at least two compounds of the sample with the analytical column; and
detecting the at least two compounds exiting the analytical column.

26. The method of claim 25, wherein the detector is a mass spectrometer.

27. The method of claim 25, wherein the carrier gas includes He or $H_2$.

28. The method of claim 25, wherein the auxiliary gas includes $N_2$, Ar, or $H_2$.

29. The method of claim 25, wherein the flow restrictor is sized to provide a volume of carrier gas sufficient to prevent the auxiliary from entering the analytical column during the resolving phase.

30. The method of claim 25, wherein the flow restrictor is sized to provide a volume of carrier gas that exceeds the operating flow of the analytical column by a factor of at least about 1.5.

31. The method of claim 25, wherein the flow restrictor is sized to provide a volume of carrier gas that exceeds the operating flow of the analytical column by a factor of not more than about 10.

* * * * *